United States Patent [19]

Redmond et al.

[11] Patent Number: 4,781,680
[45] Date of Patent: Nov. 1, 1988

[54] RESEALABLE INJECTION SITE

[75] Inventors: Russell Redmond, Goleta; Claude Vidal, Santa Barbara, both of Calif.

[73] Assignee: VIR Engineering, Goleta, Calif.

[21] Appl. No.: 20,725

[22] Filed: Mar. 2, 1987

[51] Int. Cl.⁴ .............................................. A61M 11/00
[52] U.S. Cl. ........................................ 604/93; 604/86; 604/891.1; 604/185; 604/8
[58] Field of Search ................. 604/93, 175, 185, 891, 604/86, 8-10, 190, 212, 891

[56] References Cited

U.S. PATENT DOCUMENTS

| | | | |
|---|---|---|---|
| 3,951,147 | 4/1976 | Tucker et al. | 604/891 |
| 4,133,441 | 1/1979 | Mittleman et al. | 604/86 |
| 4,496,343 | 1/1985 | Prost et al. | 604/86 |
| 4,559,033 | 12/1985 | Stephen et al. | 604/185 |
| 4,634,424 | 1/1987 | O'Boyle | 604/86 |
| 4,634,427 | 1/1987 | Hannula et al. | 604/93 |
| 4,681,560 | 7/1987 | Schulte et al. | 604/8 |

OTHER PUBLICATIONS

*Scientific American*-by Perry Blackshear titled "Implantable Drug Delivery Systems", Dec. 1979, pp. 66-73.

Primary Examiner—C. Fred Rosenbaum
Assistant Examiner—Colleen M. Reilly
Attorney, Agent, or Firm—James E. Brunton

[57] ABSTRACT

A subcutaneous access site to aid in the delivery of chemotherapeutic or analgesic drugs to the blood stream or to any body cavity. The device embodies a specially supported septum which exhibits exceptional resealing characteristics. In this regard, the device includes a rigid inner ring adapted to create uniform circumferential compression on the septum member to enhance site resealing even when standard twelve degree beveled hypodermic syringe needles are used. Additionally, the device is uniquely configured to give immediate feedback to the caregiver if the needle misses the target, thereby minimizing accidental subcutaneous injections.

14 Claims, 3 Drawing Sheets

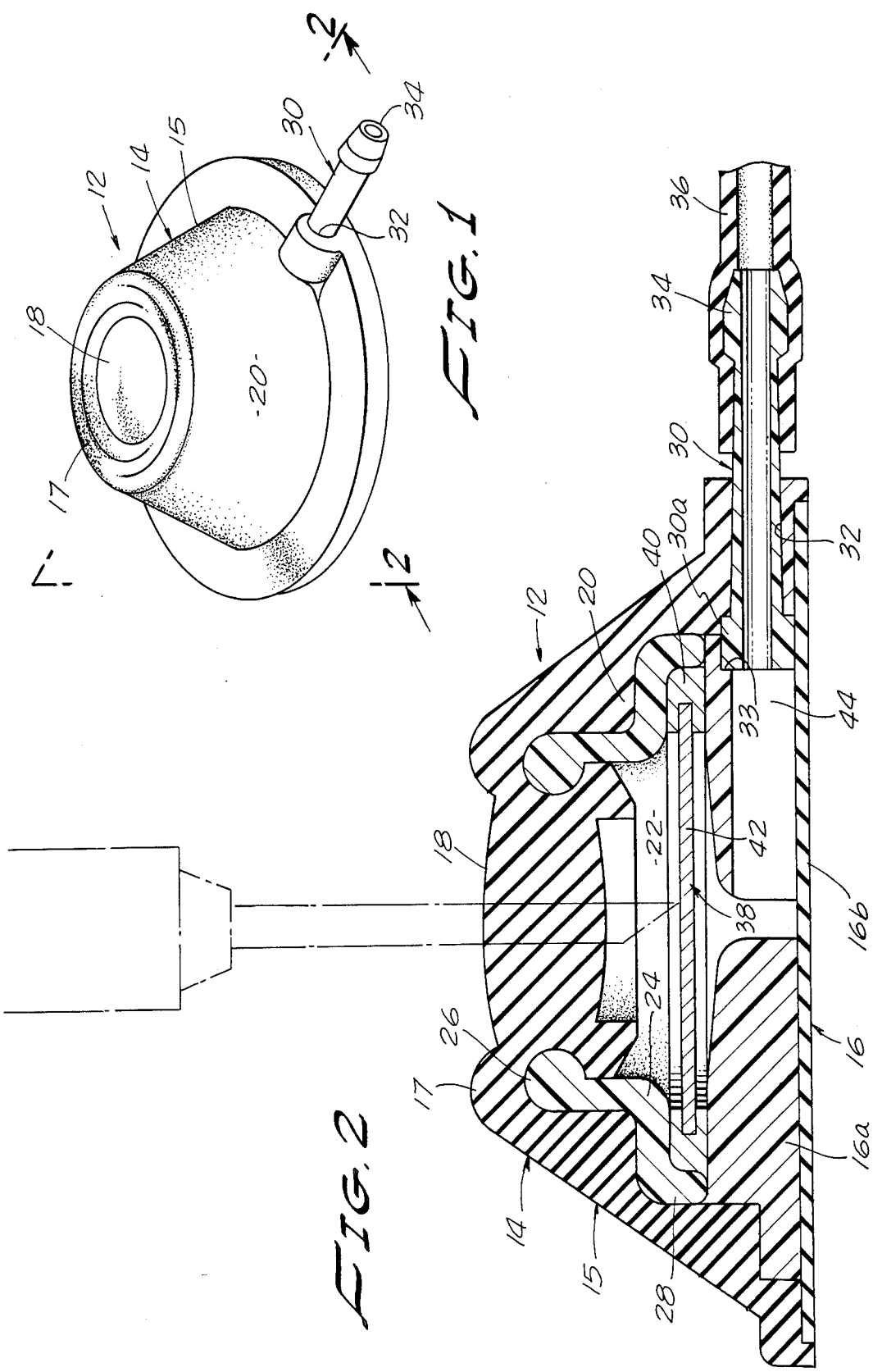

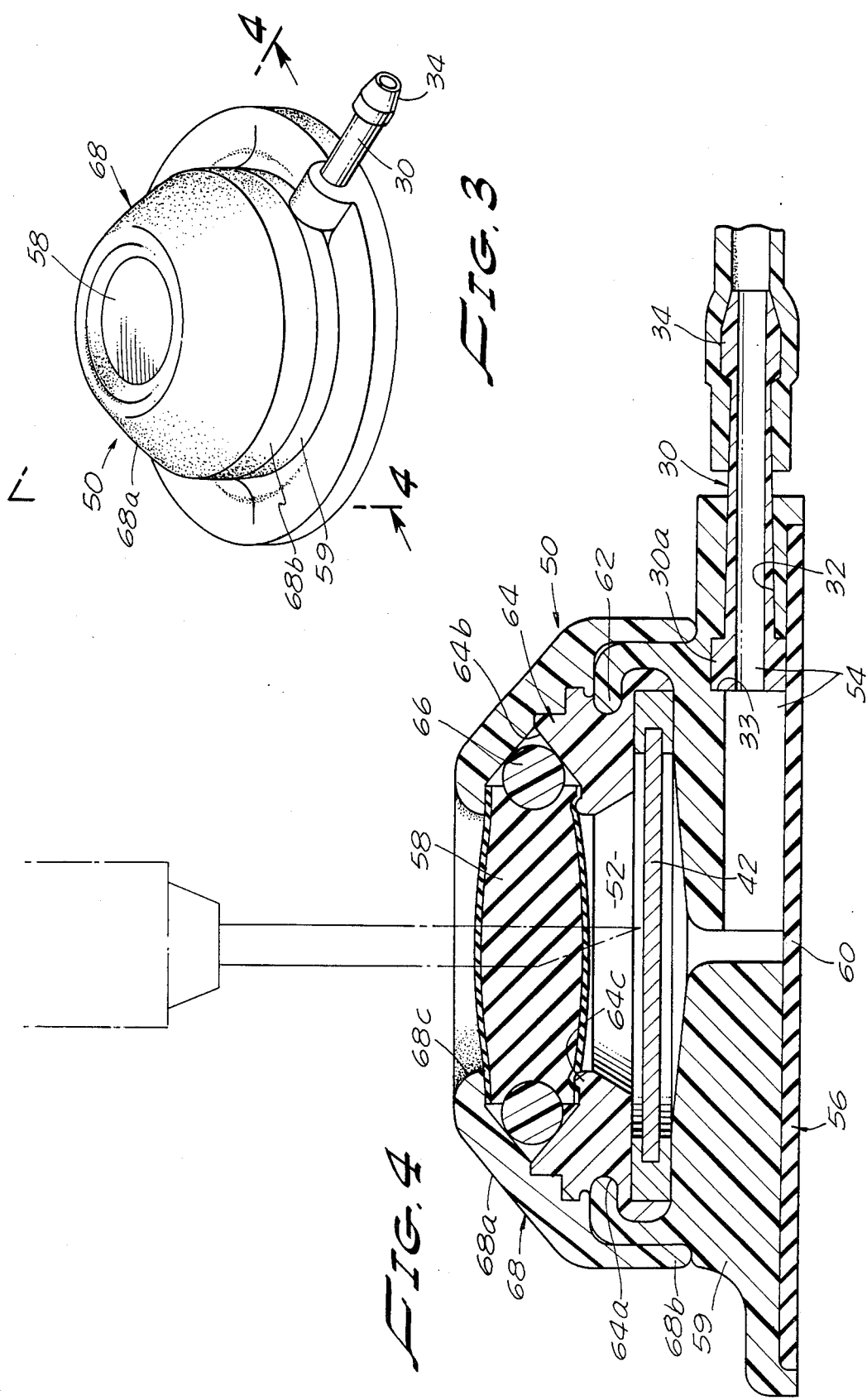

RESEALABLE INJECTION SITE

BACKGROUND OF THE INVENTION

1. Field of the Invention—

The present invention relates generally to injection sites for use in the injection of fluids into the body. More particularly, the invention concerns a subcutaneous access site for repeated intermittent vascular and spinal injection or continuous infusion of drugs and fluids.

2. Discussion of the Prior Art—

Blood sampling, drug delivery and fluid replacement frequently require repeated access to the vascular system of the body. Typically, access to the vascular system is gained using a hypodermic syringe. Repeated injections by means of repetitive punctures is obviously undesirable, especially in fragile vessels or difficult to reach body regions. For this reason, various types of subcutaneous access sites have been devised in the past.

One relatively early prior art implant device for the injection and withdrawal of fluids is disclosed in U.S. Pat. No. 3,310,051 issued to Schulte. A later U.S. Pat. No. 4,190,040, issued to Schulte, discloses a resealable puncture housing for surgical implantation. This latter device is adapted to receive repeated hypodermic punctures through the skin and into the housing of the device. A subcutaneous peritoneal injection catheter is disclosed in U.S. Pat. No. 4,405,305 issued to Stephen et al.

In using subcutaneous access devices for the injection of drugs, great care must be taken to insure that the hypodermic needle punctures the septum of the device and is not deflected away by the supporting structure of the device so that the drug is accidentally introduced into the subcutaneous pocket within which the device is located. With certain drugs, such as chemotherapeutic drugs, this type of extravasation can be extremely serious. In a similar vein, certain prior art devices tend to leak around the puncture site, or around the internal reservoir of the device, particularly under conditions of back pressure experienced during the injection step. This leakage can also result in a dangerous drug or a caustic fluid accidentally reaching the subcutaneous implantation pocket and the body areas surrounding the injection site.

In certain of the earlier prior art subcutaneous access devices the basic design and choices of construction materials were poor. This resulted in ineffective sealing about the needle and substantial fluid leakage of the septum after relatively few punctures. Additionally, dangerous material degredation was frequently observed as a function of time. Further, the septum, or injection membrane of the prior art devices, was typically supported in a manner which allowed axially directed stretching of the membrane which worked against, rather than improving, the resealing characteristics of the septum after puncture by the needle of the syringe.

Other drawbacks of the prior art subcutaneous access devices include difficulty of surgical implantation, patient discomfort and errosion of interface tissue as a result of the bulk and configuration of the devices. Additionally, in many instances, the prior art devices were constructed of rigid plastic or metal components which markedly contributed to patient discomfort and tissue damage.

The device of the present invention uniquely overcomes the aforementioned drawbacks of the prior art devices by providing a novel subcutaneous injection site which is specially designed to provide superior septum resealing characteristics and to provide immediate feedback to the care giver if the needle misses the septum target area.

SUMMARY OF THE INVENTION

It is an object of the present invention to provide a highly reliable, automatically resealable subcutaneous access site to aid in the introduction and withdrawal of fluids into the body.

More particularly, it is an object of the present invention to provide a subcutaneous access site to aid in the delivery of chemotherapeutic or analgesic drugs to the blood stream or to any body cavity.

Another object of the invention is to provide a device of the aforementioned character which is easy to use, embodies a large septum target area and a specially supported septum which exhibits exceptional resealing characteristics. In this regard, the device embodies a rigid inner ring adapted to create uniform circumferential compression on the soft resealing septum member to enhance site resealing even when standard twelve degree beveled needles are used.

A further object of the invention is to provide a novel resealable injection site which is uniquely configured to give immediate feedback to the caregiver if the needle misses the target, thereby minimizing accidental subcutaneous injections. More particularly, the device embodies a soft outer dome which is bonded to the rigid inner ring in such a way that if the needle misses the target area, the tip of the needle will penetrate through the outer dome to the interface of the ring and then stop. If the user attempts to inject fluid, an immediate buildup of pressure within the syringe will result as the fluid tries to push the soft dome away from the ring. This pressure buildup will immediately signal the user that the injection target has been missed.

Still another object of the present invention is to provide a device as described in the preceding paragraphs which comprises a soft biocompatible exterior and a configuration that improves patient comfort and minimizes tissue errosion.

BRIEF DESCRIPTION OF THE DRAWINGS

FIG. 1 is a generally perspective view of one form of the injection site of the invention.

FIG. 2 is a greatly enlarged cross-sectional view taken along lines 2—2 of FIG. 1.

FIG. 3 is a generally perspective view of an alternate form of injection site of the present invention.

FIG. 4 is a greatly enlarged cross-sectional view taken along lines 4—4 of FIG. 3.

DESCRIPTION OF THE INVENTION

Figure 5:
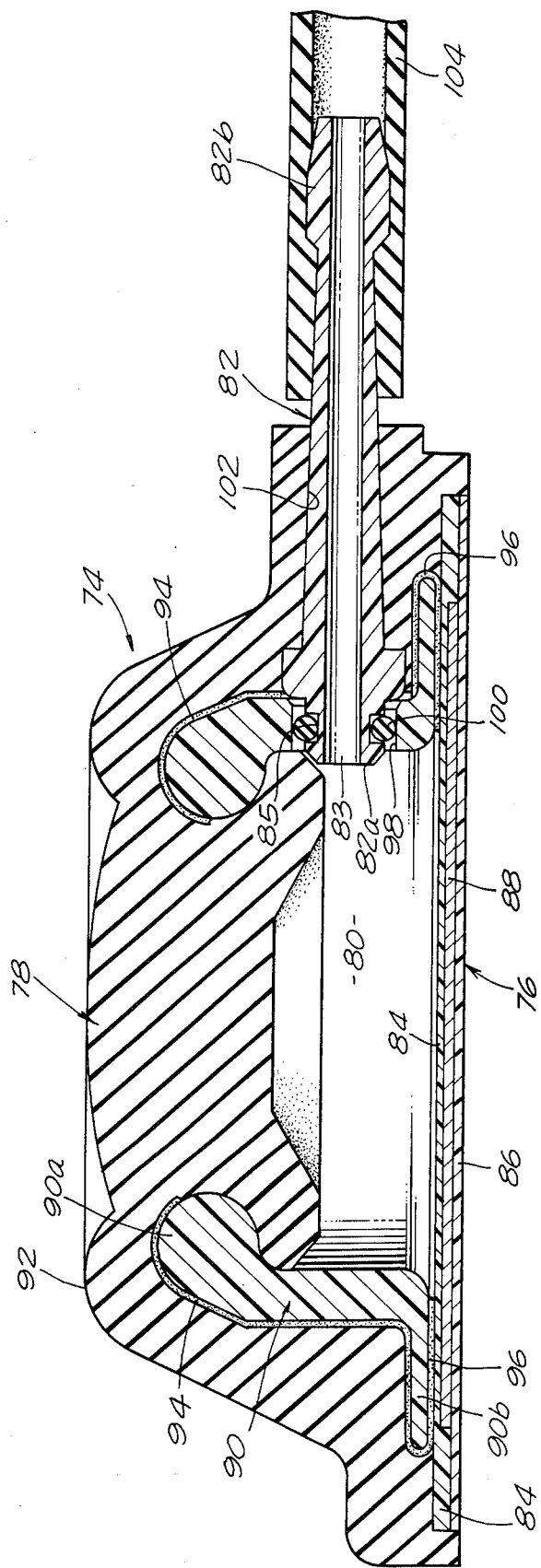
FIG. 5 is a cross-sectional view of yet another form of the injection site of the present invention.

Referring to the drawings, and particularly to FIGS. 1 and 2, the subcutaneous injection site of the form of the present invention there depicted is generally designated by the numeral 12. In this embodiment of the invention, the injection site comprises a housing 14 which includes a base assembly 16, a generally disc shaped elastomeric septum portion 18 spaced apart from base assembly 16 and continuous side walls 20. Side walls 20 interconnect the base assembly 16 with the septum portion 18 to define an internal chamber 22 which is disposed intermediate base assembly 16 and septum portion 18. In the embodiment of the invention shown in FIGS. 1 and 2, base assembly 16 comprises a structural support member 16a which may be constructed of rigid plastic or other suitable material and an enlarged diameter, generally disc-shaped base element 16b which preferably is formed of an elastomeric material such as a reinforced silicon. Base element 16b can be interconnected with support member 16a by any suitable means such as bonding with an appropriate adhesive.

To enable interconnection of the resealable injection site with a fluid conduit such as a catheter, connector means are associated with the housing and particularly with base assembly 16 for providing a fluid flow path between internal chamber 22 and the exterior of the housing. In the embodiment of the invention shown in FIGS. 1 and 2, the connector means is provided in the form of an elongated tubular connector member 30, one end 30a of which is receivable through a bore 32 provided in side walls 20. As best seen in FIG. 2, end 30a of member 30 is axially located within bore 32 by means of engagement with a shoulder 33 formed on member 16a. Structural member 16a of base assembly 16. Connector 30 is provided at its opposite end 34 with an enlarged diameter, inwardly tapering portion for receipt thereover of a flexible fluid conduit 36 which may take the form of a catheter or other tubular element.

Also forming a part of the subcutaneous injection site of the present invention is a filtering means provided in the form of a filter assembly 38. Filter assembly 38 comprises a ring shaped portion 40 which is disposed intermediate cup shaped member 28 of the compression means and structural member 16a of the base assembly 16. Ring shaped portion member 40 functions to support a filter element 42 which is preferably provided as a micron filter constructed of sintered stainless steel. With this arrangement, the filter means is disposed intermediate internal chamber 22 and the fluid flow passageway of the apparatus, which is here defined by connector element 30, which communicates with an internal bore 44 provided in support element 16a of base assembly 16. With the filter means positioned within the apparatus in the manner shown in FIG. 2, fluid flowing between internal chamber 22 and exterior of the device will be appropriately filtered by the filter element 42.

Forming another important aspect of the injection site of the present invention is the configuration of the housing 14 of the apparatus. As best seen in FIG. 2, housing 14 comprises side walls which include a generally frustoconically shaped intermediate portion 15 which circumscribes the compression means and internal chamber 22. Intermediate portion 15 terminate in an upstanding portion shown here as an upper dome-shaped portion 17 which is at least partially superimposed over the rigid ring portion 26 of the compression means of the invention. With this unique construction, if the needle of the hypodermic syringe misses the septum target area, the tip of the needle will penetrate through the outer dome to the interface of the compression means, or cup-shaped member 24, and will then stop. If the user attempts to inject fluid with the needle in this position, an immediate buildup of pressure within the syringe will result as the fluid tries to push the soft dome away from the cup-shaped member 24. This pressure buildup will immediately signal the caregiver that the injection target has been missed. The caregiver will then withdraw the needle and reinsert it until the needle correctly penetrates the septum target area in the manner shown by the phantom lines in FIG. 2 and bottoms out against the filter element 42 of the filter means. With the needle in this position, pressure exerted on the hypodermic syringe will cause the ejection of fluid from the syringe into internal chamber 22 without any undue buildup of backpressure. The caregiver will then be assured that the hypodermic syringe has penetrated the septum target area and is positively in communication with the internal chamber 22. In this way, accidental injection of harmful fluids, such as drugs or caustic solutions, into the subcutaneous area surrounding the injection site will be positively avoided.

It should be understood that upper portion 17 need not be dome shaped in all cases. In instances where two injection sites are used, for example, in a situation wherein one catheter goes to a specific organ and another goes to the venous system, or as in the case of treating chronic pain, where one catheter may lead into the spine, it is difficult to tell which injection site is for which injection. In such situations, a nonround external shape may be used for the upstanding portion of one of the injection sites. This non-round site may take the shape of a truncated circle with flattened sides, a triangular shape, or a rectangular shape with the sides curved inward or other suitable shapes. In this way, two different injection sites can readily be distinguished by palpating the different external shapes.

Turning to FIGS. 3 and 4, another form of the injection site of the present invention is there illustrated. The configuration of this second form of the invention is generally similar to that previously described and like numerals are used to identify like components. More specifically, while the filtering and connector means are the same as previously described, the configuration of the housing, the septum and the compression means is slightly different. As best seen in FIG. 4, the injection site of this embodiment of the invention comprises a hollow housing assembly 50, including an internal chamber 52 and a fluid passageway 54 interconnecting internal chamber 52 with a connector member 30 having a fluid passage leading to the exterior of housing 50.

In the form of the invention shown in FIGS. 3 and 4, housing assembly 50 comprises a base assembly 56 which is disposed on one side of internal chamber 52 and a generally disc or circular shaped membrane 58 disposed on the opposite side of chamber 52. As in the previously described embodiment, a compression means is mounted within the housing assembly 50 for exerting uniform radially inwardly directed compressive forces on membrane, or septum, 58. Base assembly 56 comprises a structural support member 59 and a generally planar shaped member 60 which is connected thereto by bonding or other suitable means. Structural support member 59 includes a radially inwardly directed circumferentially extending proturberance 62, the purpose of which will be discussed hereinafter.

The compression means of this second embodiment of the invention comprises a generally annular shaped member 64 having a circumferentially extending groove 64a which is adapted to closely receive proturberance 62 of structural support member 59. A split ring 66 rests upon an inwardly sloping surface 64b formed on member 64 and, in a manner presently to be described, functions to exert radially inward compressive forces on membrane 58.

Forming another part of the housing assembly of the injection site of the invention shown in FIG. 4 is cup-shaped means 68 which is carried by the base assembly 56 and which surrounds the compression means and at least the peripheral portion of the membrane or septum 58. This closure means functions to seal the internal chamber 52 of the device with respect to atmosphere and is hereprovided in the form of a generally cup shaped member 68 having a frustonconically shaped central portion 68a and a downwardly depending skirt portion 68b. Skirt portion 68b is disposed in close engagement with support member 59 of the base assembly 56 in the manner illustrated in FIG. 4. At the upper end of cup-shaped member 68 is a downwardly depending lip 68c which presently engages membrane 58 and functions to securely clamp the membrane in position against an upwardly extending circumferential proturberance 64c formed on base member 64. Cup-shaped member 68, in this configuration, also functions to securely clamp split ring 66 between the inner surfaces of the cup-shaped member and the inwardly sloping surface 64b of base member 64 and is so constructed and arranged as to cause the split ring to exert a uniform circumferential pressure on membrane 58. With this construction, when the needle, shown in the phantom lines of FIG. 4, penetrates the septum 58, no leakage will occur between the needle and the septum. Additionally, when the needle is removed, the circumferential compressive forces acting on the septum will markedly enhance its resealing characteristics.

Turning to FIG. 5 of the drawings, a third embodiment of the subcutaneous injection site of the invention is thereshown. In this embodiment of the invention, the injection site comprises a housing 74 which includes a base assembly 76 and, like the previously discussed embodiments, includes the important compression means for exerting circumferential forces on the central portion 78 of housing 74, which central portion comprises the septum portion of the injection site. Disposed between central portion 78 of the housing and base assembly 76 is an interior chamber 80 which is in fluid communication with the exterior of the housing via a connector element, or lumen, 82 having a central fluid passageway 83.

Base 76 is of a laminate construction having an upper disc shaped base element 84, a lower disc shaped element 86 and a needle guard 88 disposed intermediate base discs 84 and 86. Needle guard 88 is preferably constructed of stainless steel and serves to indicate to the caregiver that the needle of the hypodermic syringe has penetrated the septum and entered the internal chamber 80. Lower base disc 86 is preferably formed of an elastomeric material such as reinforced silicone and is securely bonded to upper base disc 84 which, in turn, is securely bonded to the lower portion of housing 74 in the manner shown in FIG. 5.

In the instant form of the invention the compression means is provided as a generally annular shaped member 90 which is generally J-shaped in cross-section. Member 90 includes an upper ring shaped portion 90a and a lower radially outwardly extending base leg portion 90b.

The exterior walls of the central portion of housing 74 are generally frustoconical in shape and the inner wall is configured to closely conform to the shape of the outer wall of annular shaped member 90. The upper portion 92 of housing 74 is generally dome shaped and is constructed from a soft elastomer such as silicone. This dome shaped portion cooperates with the compression member in the manner previously described to give notice to the caregiver if the needle of the hypodermic syringe misses the septum target area 78.

An important advantage of the injection site of this third embodiment of the invention over prior art injection sites is that it can reseal and be totally leak free even under relatively high injection pressures. This important feature is achieved by creating an internal pressure chamber which can only communicate with atmosphere through the connector member, or lumen, 82. Therefore, when the septum portion 78 is punctured, the syringe can create high internal pressures as may be required to overcome downstream resistance without communicating that pressure to the junction between the compression means and the upper dome shaped portion 92. To create this positively sealed internal pressure chamber 52, a broad, continuous adhesive seal 94 is formed between the annular member 90 and the inner walls of housing 74. A broad adhesive seal 96 is also provided between the upper surface of base disc 84 and the lower surface of the base leg 90b of member 90. Any commercially available adhesive and suitable primer adapted the sealable for interconnection of elastomeric to metal or plastic materials will suffice to provide the broad adhesive seals 94 and 96.

Further positive sealing the internal chamber 80 relative to atmosphere is sealing means for sealably interconnecting connector member, or lumen, 82 with the annular or cup-shaped member 90 which comprises the compression means of this embodiment of the invention. As indicated in FIG. 5, member 90 is provided with a radially extending bore or passage 98 which receives the inboard end 82a of connector member 82. Inboard end 82a of connector member is provided with a circumferential groove 85 to receive an elastomeric O-ring 100 which comprises the sealing means of this third form of the device of the present invention.

As indicated in FIG. 5, connector member 82 is closely received through a bore 102 formed in housing 74. Provided at the outboard end of connector 82 is an enlarged diameter portion 82b which is receivable within a fluid passageway formed in an elongated fluid conduit such as a catheter 104.

Once again, the compression means, or ring portion, 90a of annular member 90 is constructed so as to impart a uniform radially inwardly directed circumferential compressive force on the septum portion 78 of the housing 74. As previously discussed, this circumferential force exerted on the septum substantially enhances the resealing characteristics of the septum.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

I claim:
1. A subcutaneous injection site, comprising:
 (a) a housing, including:
  (i) a base;
  (ii) a generally disc shaped elastomeric septum spaced apart from said base;
  (iii) continuous side walls constructed of a relatively soft elastomeric material interconnected with said base and with said septum to define an internal chamber disposed intermediate said base and said septum said side walls including a dome shaped portion;

(iv) compression means for exerting circumferential compression on said disc shaped elastomeric septum, said compression means comprising a rigid ring surrounding said generally disc shaped elastomeric septum and disposed interiorly of said continuous side walls and beneath said dome shaped portion;

(b) connector means associated with said housing for providing a fluid flow path between said internal chamber and the exterior of said housing, and (c) filter means disposed between said internal chamber and said connector means for filtering fluids flowing between said internal chamber and the exterior of said housing, said filter means comprising a rigid sintered metal element.

2. A subcutaneous injection site having a hollow housing including an internal chamber and a fluid passageway interconnecting said internal chamber with the exterior of said housing, said housing comprising:

(a) a base disposed on one side of said internal chamber;

(b) a generally circular shaped membrane constructed from an elastomer disposed on the opposite side of said internal chamber;

(c) compression means supported by said base for exerting uniform radially inwardly directed compressive forces on said membrane, said compression means comprising a generally annular shaped member carried by said base and a split ring carried by said annular shaped member; and (a) closure means carried by said base and surrounding said compression means and at least the periphery of said membrane for sealing said internal chamber relative to atmosphere.

3. An injection site as defined in claim 2 in which said split ring is held in place between a portion of said closure means and a portion of said annular shaped member.

4. An injection site as defined in claim 2 in which said compression means comprises a generally cup-shaped member having an annular shaped portion and an interconnected skirt portion disposed in engagement with said base.

5. An injection site as defined in claim 4 in which said membrane is generally disc shaped and is constructed from a silicone material.

6. An injection site as defined in claim 4 in which said membrane is constructed from a silicone, latex laminate.

7. An injection site as defined in claim 4 in which said closure means further comprises a generally dome shaped circumferentially extending portion.

8. An injection site as defined in claim 4 in which the fluid passageway interconnecting said internal chamber with the exterior of said housing is provided by a tubular connector member carried by said housing.

9. An injection site as defined in claim 8 further including sealing means for sealably interconnecting said connector member with said generally cup-shaped member.

10. An injection site as defined in claim 9 in which said cup-shaped member is provided with a passageway in communication with said internal chamber and in which said sealing means comprises an elastomeric O-ring sealably receivable within said passageway of said cup-shaped member.

11. A subcutaneous injection site having a hollow housing including an internal chamber and a fluid passageway interconnecting said internal chamber with the exterior of said housing, said housing comprising:

(a) a base disposed on one side of said internal chamber;

(b) a generally circular shaped membrane constructed from an elastomer disposed on the opposite side of said internal chamber;

(c) compression means supported by said base for exerting uniform radially inwardly directed compressive forces on said membrane said compression means comprising a generally cup-shaped member having an annular shaped portion and an interconnected skirt portion disposed in engagement with said base, said cup-shaped member further having a passageway in communication with said internal chamber;

(d) a tubular connector member carried by said housing, said member providing the fluid passageway interconnecting said internal chamber with the exterior of said housing; and (e) sealing means for sealably interconnecting said tubular connector member with said generally cup-shaped member.

12. A subcutaneous injection site as defined in claim 11 further including filter means disposed between said internal chamber and said fluid passageway for filtering fluids flowing between said internal chamber and the exterior of said housing.

13. A subcutaneous injection site as defined in claim 12 in which said filter means comprises a rigid sintered metal element substantially impenetrable by hypodermic needle.

14. A subcutaneous injection site for use with a hypodermic needle for delivery of fluids to the body, comprising:

(a) a housing, including:
 (i) a base;
 (ii) a generally disc shaped elastomeric septum spaced apart from said base said septum being penetrable by the hypodermic needle;
 (iii) continuous side walls constructed of a relatively soft elastomeric material interconnected with said base and with said septum to define an internal chamber disposed intermediate said base and said septum said side walls including a dome shaped portion;
 (iv) a rigid ring surrounding said generally disc shaped elastomeric septum and disposed interiorly of said continuous side walls and beneath said dome shaped portion; said rigid ring being so constructed and arranged as to continuously exert a radially inwardly directed, uniform compressive force on said elastomeric septum whereby resealing is enhanced following penetration of said elastomeric septum by the hypodermic needle;

(b) connector means associated with said housing for providing a fluid flow path between said internal chamber and the exterior of said housing, and (c) closure means carried by said base and surrounding said compression means and at least the periphery of said membrane for sealing said internal chamber relative to atmosphere.

* * * * *